(12) United States Patent
Broy et al.

(10) Patent No.: US 6,524,740 B1
(45) Date of Patent: Feb. 25, 2003

(54) METHOD AND APPARATUS FOR IMPROVED GAS SENSOR

(75) Inventors: Stephen H. Broy, Riverside, CA (US); Austin J. Patrizio, Mt. Laurel, NJ (US)

(73) Assignee: Teledyne Technologies Incorporated, Los Angeles, CA (US)

( * ) Notice: Subject to any disclaimer, the term of this patent is extended or adjusted under 35 U.S.C. 154(b) by 0 days.

(21) Appl. No.: 09/531,707

(22) Filed: Mar. 21, 2000

(51) Int. Cl.[7] .............................................. H01M 10/48
(52) U.S. Cl. .......................... 429/61; 204/424; 204/429
(58) Field of Search ............................. 429/22, 25, 34, 429/61; 204/424, 429

(56) References Cited

U.S. PATENT DOCUMENTS

| 4,379,741 A | | 4/1983 | Sano et al. | |
|---|---|---|---|---|
| 4,406,770 A | * | 9/1983 | Chan et al. | 204/406 |
| 5,334,295 A | | 8/1994 | Gallagher et al. | |
| 5,336,390 A | * | 8/1994 | Busack et al. | 204/431 |
| 5,372,696 A | * | 12/1994 | Kiesele et al. | 204/412 |
| 5,395,507 A | * | 3/1995 | Aston et al. | 204/431 |
| 5,498,487 A | * | 3/1996 | Ruka et al. | 429/20 |
| 5,728,289 A | | 3/1998 | Kirchnavy et al. | |
| 5,830,337 A | * | 11/1998 | Xu | 204/400 |
| 5,886,248 A | | 3/1999 | Paulus et al. | |
| 5,942,092 A | | 8/1999 | Weyl et al. | |
| 6,099,708 A | * | 8/2000 | Mallory et al. | 204/412 |
| 6,305,214 B1 | * | 10/2001 | Schattke et al. | 73/31.05 |

FOREIGN PATENT DOCUMENTS

| EP | 0205399 A2 | 12/1986 |
|---|---|---|
| EP | 0786660 A2 | 7/1997 |
| GB | 2178540 A | 2/1987 |
| GB | 2326485 A | 12/1998 |
| WO | WO99/22229 | 5/1999 |

* cited by examiner

*Primary Examiner*—Patrick Ryan
*Assistant Examiner*—M. Wills
(74) *Attorney, Agent, or Firm*—Kirkpatrick & Lockhart LLP

(57) ABSTRACT

A gas sensor comprising a housing and arranged such that a gas flow resistant member engages the housing and is sealably positioned to restrict the flow of gas into the opening leading to the cavity. Where the sensor is installed into a cell holder of the gas analyzer, the cell holder may include a gas flow resistant member opener to open the gas resistant member after being contained therein. In this way, the amount of gas to which the sensor is exposed during the transition period is substantially reduced. Accordingly, the amount of gas that diffuses into the electrolyte solution that would, otherwise, adversely affect the accurate and precise measurement of low concentrations of gas at the early stages of operation, is greatly diminished. As a result, the recovery time required for the excess gas to diffuse from the electrolyte is substantially reduced.

45 Claims, 15 Drawing Sheets

METHOD AND APPARATUS FOR IMPROVED GAS SENSOR

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

This invention relates to an improved gas sensor and its method of manufacture, and more particularly to a gas sensor having a protective member to restrict the flow of gas into the sensor.

2. Brief Description of the Invention Background

FIG. 1 illustrates a typical micro fuel cell oxygen sensor 110 such as, for example, Teledyne Analytical Instruments' B2 sold by Teledyne Electronic Technologies, City of Industry, Calif. The oxygen sensor 110 consists of a cathode 102 and an anode 104 sealed in a housing 106 filled with appropriate electrolyte solution. Oxygen diffuses into the interior of the sensor housing 106 through a thin sensing membrane 108. A flexible expansion membrane 112 at the opposite end of the sensor 110 permits expansion or contraction of the electrolyte volume. The sensing membrane 108 is sealed in place by means of press fit. The expansion membrane 112 is sealed in place by heat seal. Reduction of oxygen at the cathode 102 causes current to flow from the cathode 102 to the anode 104 through an externally connected sensing circuit (not shown).

Present demands on gas analyzers require that the gas sensors that they employ, such as the B2 model described above, effectively measure very low concentrations of gas. For example, it is typically the case that oxygen gas must be measured in the parts per million range. Accordingly, the gas sensor must be extremely sensitive to very low level gas concentrations.

Due to its extreme sensitivity, the gas sensor and, particularly, the cathode and sensing membrane, must be protected from high ambient gas levels during transport. This is so because exposure of the sensor to, for example, high levels of oxygen for an extended period, results in the electrolyte accumulating excessive oxygen levels. These excessive levels inhibit accurate measurement of gas at low levels due to an error signal associated with the level of dissolved oxygen in the electrolyte. To reduce the effect of this exposure, it is known to seal the sensor for shipment in double protective packaging 120 such as, for example, sealable, metalized plastic bags, having an inert (e.g. oxygen-free) environment (FIG. 2).

The packaging provides acceptable protection from, for example, ambient oxygen levels, while the gas sensor is being shipped from the manufacturing facility to the buyer. As illustrated in FIGS. 3–5, when the gas sensor is received and ready for use, the gas sensor 110 is removed from the zero oxygen packaging 120 for positioning between a cap portion 125 and a cavity portion 130 of the cell block for installation into the analyzer 130 (FIG. 5). The cell block exposes the sensor to only the sample gas stream, and provides hermetic electrical connections to the cathode, anode, and other necessary electrical terminals of the sensor.

During the transition period from the zero oxygen packaging to the analyzer, however, the gas sensor is exposed to ambient air and is, thus, flooded with, for example, high levels of oxygen (typically present in ambient air in an amount of about 21 percent on a volume basis). This exposure introduces large amounts of oxygen into the electrolyte which must slowly diffuse from the electrolyte before the gas sensor can accurately and precisely measure extremely low levels of oxygen. The time required for the high ambient gas levels to diffuse from the sensor is known as the recovery time, and is typically on the order of several hours. During this time, the user typically either must vent the product being qualified by the analyzer to atmosphere, switch to a liquid backup supply, or utilize another inline analyzer that is capable of immediately measuring the gas stream with the required accuracy. All of these options have relatively high associated costs.

Existing gas sensors, such as the B2 sensor 110 of FIG. 1, have little or no ability to prevent the flood of gas, particularly oxygen, into the gas sensor during the transition period. Accordingly, gas analysis through the gas sensor is delayed for at least several hours in order for the oxygen gas to diffuse from the electrolyte, and for the gas levels inside the gas sensor to normalize. As with other prior art sensors, this delay inhibits the effective use of the analyzer to monitor the gaseous stream at the early stages of gas analysis, and may reduce the active life of the sensor.

Accordingly, the need exists for an improved gas sensor that limits the exposure of the sensor to gas, particularly to high concentrations of oxygen in ambient air, that may flood the sensor during the transition period, first beginning when the gas sensor is removed from the protective packaging until installation into the gas analyzer. In so doing, the recovery time needed after installation of the sensor into the analyzer would be greatly reduced.

BRIEF SUMMARY OF THE INVENTION

The present invention addresses the above-mentioned needs by providing a gas sensor comprising a housing including a cavity. The housing defines an opening into the cavity over which is sealably positioned a gas flow resistant member that engages the housing.

The present invention is also directed to a gas sensor comprising a housing including a cavity. The housing includes a first end defining an opening into the cavity. A first electrode is positioned within the cavity, and a second electrode is positioned at the opening. A sensing membrane is positioned at the opening adjacent to the second electrode, and a gas resistant member engages the first end of the housing and is sealably positioned over the opening.

The present invention is additionally directed to a gas sensor comprising a housing including a cavity. The housing defines an opening into the cavity. A means for restricting the flow of a gas into the opening engages the housing.

Furthermore, the present invention is directed to a fuel cell comprising a gas sensor constructed according to the present invention.

Moreover, the present invention is directed to a cell block comprising a cavity portion and a cap portion that are removably secured together. One of the cavity portion and the cap portion further includes a piercing member.

The present invention is also directed to a system for sensing gas comprising a gas analyzer, a cell block and a gas sensor. The analyzer defines a cavity and is sized to receive the cell block. The gas sensor is constructed according to the present invention.

A method of inhibiting the flow of gas into a gas sensor is also disclosed herein. The method includes securing a gas flow resistant member to a housing of the gas sensor, the housing including a cavity. The housing defines an opening into the cavity such that the gas flow resistant member is sealably positioned over the opening.

The present invention is also directed to a method of performing gas analysis on a gaseous stream. The method comprises inserting a gas sensor into a cell block. The gas sensor includes a housing having a cavity therein. The housing defines an opening into the sensor cavity that is sealed by a gas flow resistant member to restrict a flow of gas into the housing cavity from a region exterior to the housing cavity. The method further comprises providing fluid communication between the exterior region of the sensor cavity and the sensor cavity, inserting a cell block into the analyzer cavity, and performing gas analysis on the gaseous stream.

BRIEF DESCRIPTION OF THE SEVERAL VIEWS OF THE DRAWING

The characteristics and advantages of the present invention may be better understood by reference to the accompanying drawings, wherein like reference numerals designate like elements and in which.

DETAILED DESCRIPTION OF EMBODIMENTS OF THE INVENTION

Figure 1:
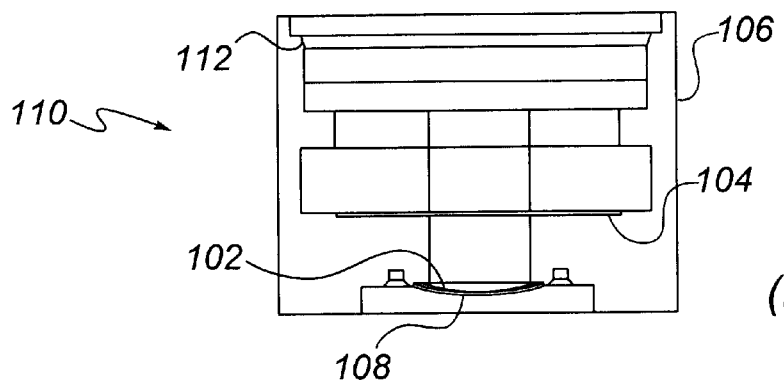
FIG. 1 is a cross-sectional view of a prior art gas sensor.
Figure 2:
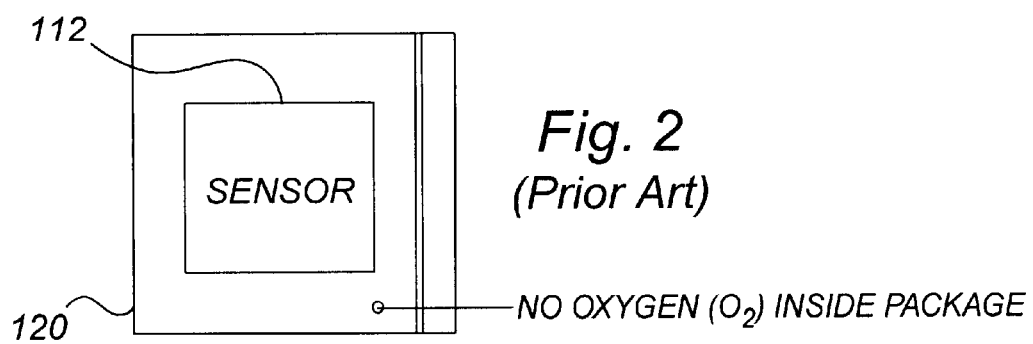
FIG. 2 is a view of the prior art gas sensor of FIG. 1 sealed in a zero oxygen packaging.
Figure 3:
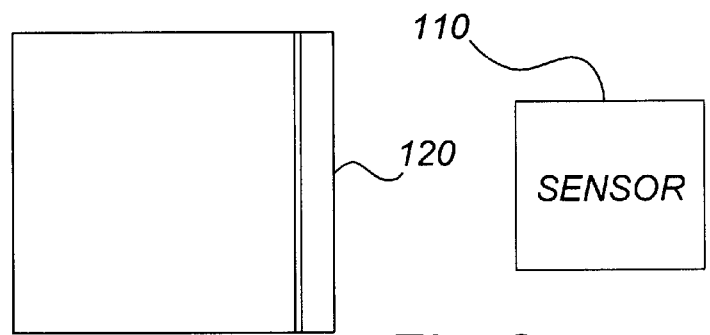
FIG. 3 is a view of the prior art gas sensor of FIG. 1 removed from the zero oxygen packaging.
Figure 4:
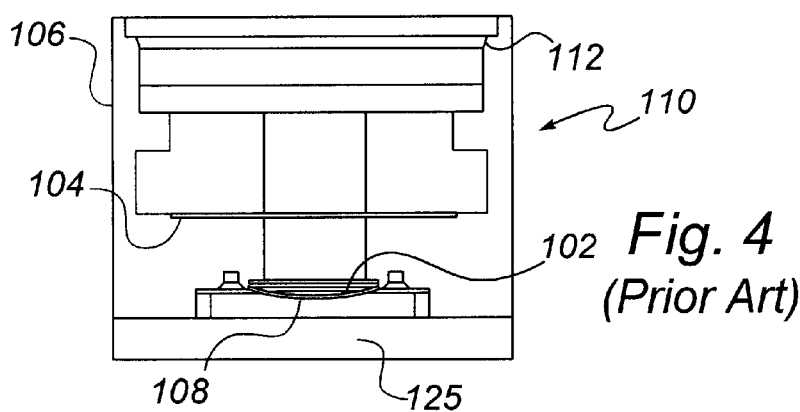
FIG. 4 is a cross-sectional view of the prior art gas sensor of FIG. 1 placed on a conventional cell holder.
Figure 5:
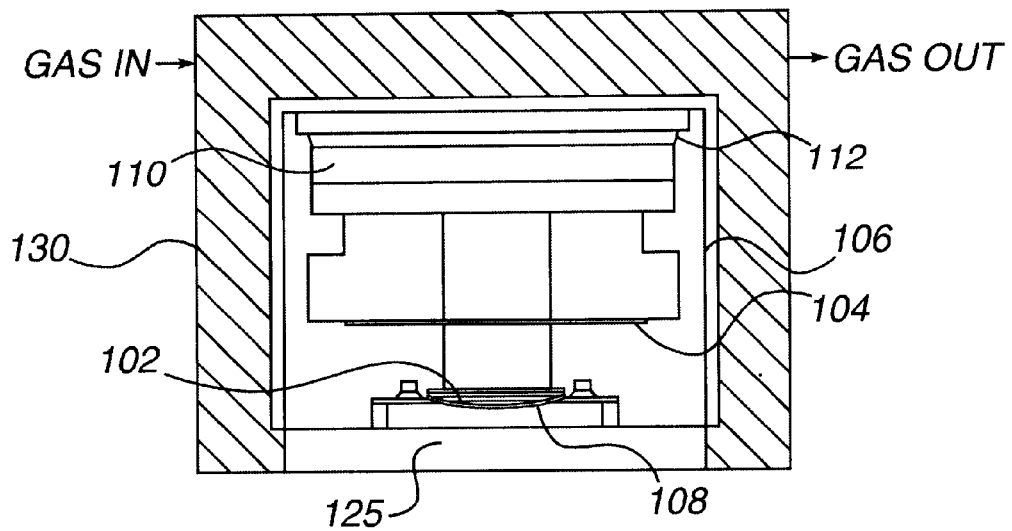
FIG. 5 is a cross-sectional view of the prior art gas sensor of FIG. 1 installed into a conventional gas sensor (cell) block analyzer.

In the present detailed description of the invention, the invention will be illustrated in the form of a gas sensor adapted for use as a sealed galvanic oxygen sensor, (such as, for example, a micro fuel cell oxygen sensor) or a polarographic oxygen sensor. It will be understood, however, that the invention is not limited to embodiment in such form and may have application in any gas sensor. Thus, while the present invention is capable of embodiment in many different forms, for ease of description this detailed description and the accompanying drawings disclose only specific forms as examples of the invention. Those having ordinary skill in the relevant art will be able to adapt the invention to application in other forms not specifically presented herein based upon the present description.

Also, for ease of description, the invention and devices to which it may be attached may be described herein in a normal operating position, and terms such as upper, is lower, front, back, horizontal, proximal, distal, etc., may be used with reference to the normal operating position of the referenced device or element. It will be understood, however, that the apparatus of the invention may be manufactured, stored, transported, used, and sold in orientations other than those described.

In addition, for ease of description, the terms "anode" and "cathode" are used herein to refer to the electrodes of the present invention. It will be understood that the terms "anode" and "cathode" are used herein to refer to the electrodes of only one embodiment of the present invention and, in particular, are used to refer to electrodes that may be incorporated as components of an oxygen sensor. It will be understood that the invention has applicability to gas sensors including electrodes identified as other than anodes and cathodes. For example, as is known in the art, other types of gas sensors may incorporate electrodes in the forms of a "sensing" or "working" electrode (the cathode) and a counter electrode (the anode), as well as reference electrode (s).

As used herein, the term "transition period" is defined as the period of time that the gas sensor is exposed to relatively high levels of gas, such as, for example, ambient air that renders the sensor not useful for accurate and precise measurement. The transition period is typically, but is not necessarily, the period of time between the removal of the gas sensor from its protective transport packaging and installation into the gas analyzer. Exposure to high levels of gas, such as oxygen, during the transition period results in a period of time that the sensor, although installed in the analyzer, is not useful for accurate and precise measurement; as used herein, this time period is identified as the "recovery time".

Typical galvanic oxygen sensors consist, in part, of a machined plastic body filled with electrolyte solution, a cathode (working electrode) manufactured from perforated sheet metal such as brass and plated with an appropriate noble metal such as, for example, rhodium, gold, or silver, and an anode (counter electrode) formed of any anode material such as, for example, compressed lead pellets. The electrolyte solution may be potassium hydroxide. A gaseous stream enters the body by diffusing through a synthetic membrane positioned at an inlet and is transported through a thin electrolyte layer to the working electrode. The oxygen is reduced to form hydroxyl ions at the working electrode. The potential applied on the cathode provides the driving force for the reduction of oxygen. Simultaneously, anode material, such as lead, is continually oxidized at the anode. Thus, the following set of electrochemical reactions occur at the cathode and the lead anode:

Cathode: $O_2 + 2H_2O + 4e^- \rightarrow 4OH^-$

Anode: $2Pb \rightarrow 2Pb^{2+} + 4e^-$

Lead oxide formed, though soluble in the potassium hydroxide electrolyte initially, will eventually deposit on the lead anode as the electrolyte becomes saturated with lead ions. When the cathode and the anode are electrically connected external to the sensor, an ionic current flows through the sensor. The current is proportional to the rate of oxygen consumption. The electric current can be measured by an electronic device. Connection between external sensing circuitry and the cathode is typically achieved by arc welding a small diameter (typically~0.01 inch) silver wire to the cathode. Connection between the same external sensing circuitry and the anode is accomplished by compressing (sintering) lead pellets around a small coil of nickel wire in an attempt to maximize the contact surface area between the wire and the lead particles.

Figure 6:
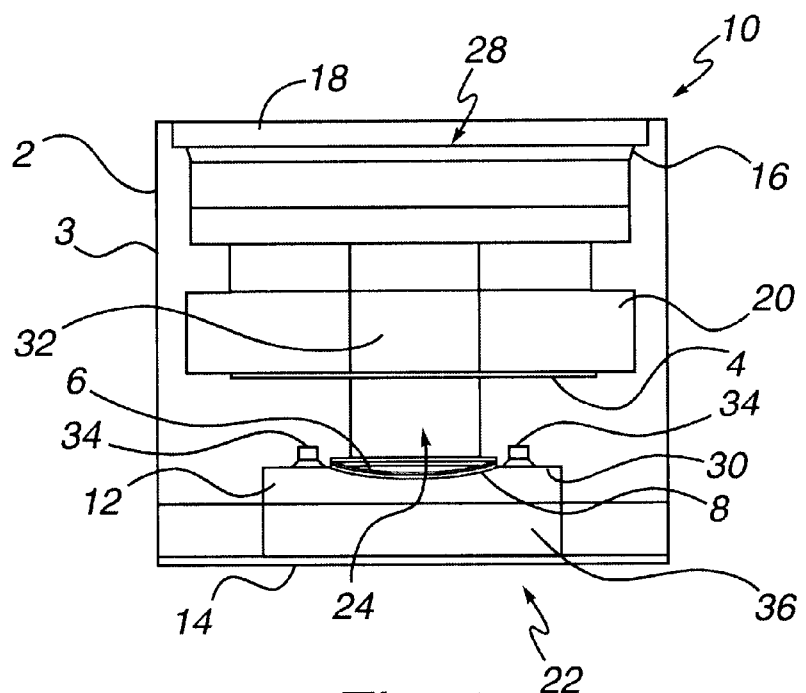
FIG. 6 is a cross-sectional view of an embodiment of the gas sensor of the present invention in the form of a micro fuel cell oxygen sensor and illustrates the arrangement of the embodiment's individual components.

Referring now to the drawings, which are for the purpose of illustrating embodiments of the invention and not for the purpose of limiting the same, FIG. 6 depicts an embodiment of a gas sensor constructed according to the present invention and in the form of a micro fuel cell oxygen sensor 10. As will be apparent from the following description, the sensor 10 improves upon the construction of the known micro fuel oxygen sensors with respect to at least the design of the sensor's sealing characteristics. The sensor 10 may include a housing 2, an anode 4, a cathode 6, a sensing membrane 8, a clamp 12, a protective member 14, an expansion or back membrane 16, and a printed circuit board 18.

Figure 7:
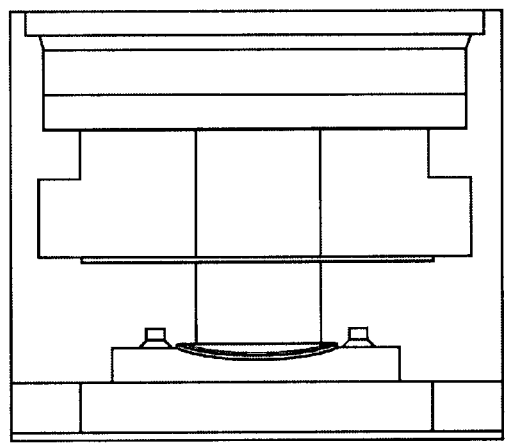
FIG. 7 is a cross-sectional view of the gas sensor of FIG. 6 and sensor holder of the present invention.
Figure 8:
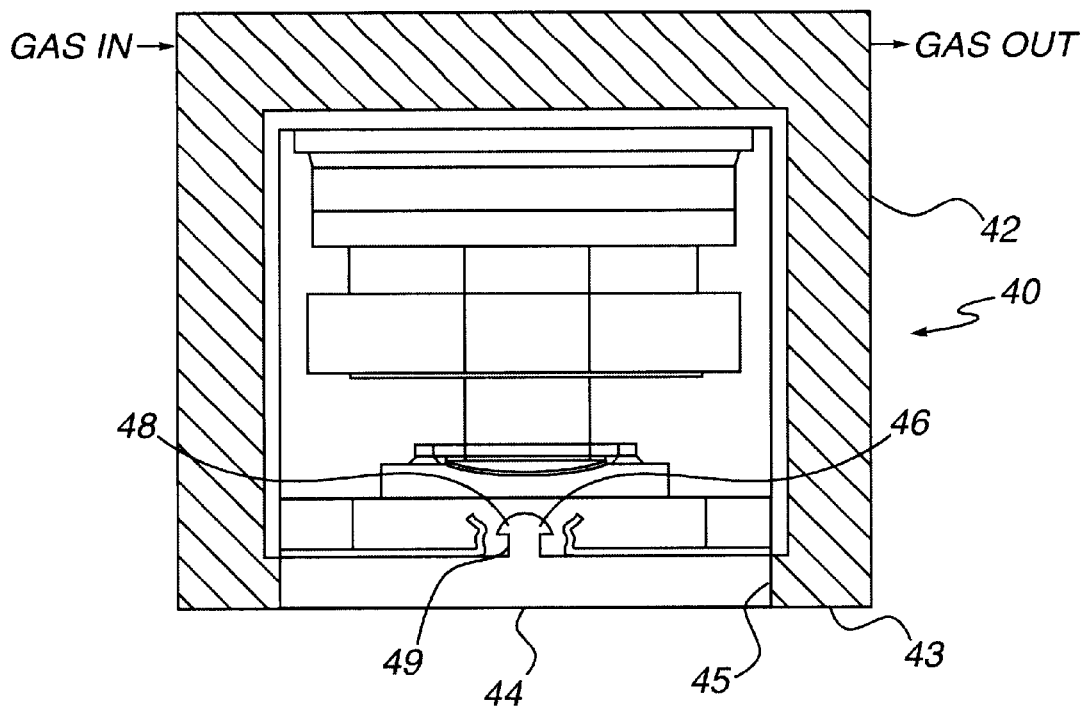
FIG. 8 is a cross-sectional view of the gas sensor of FIG. 6 and sensor holder installed into a gas analyzer.

As illustrated in FIGS. 6–8, the housing 2 may be an open ended cylinder which comprises an anode cavity 20 defined by an internal wall of the housing 2. The housing 2 may be a single formed component or may be separately formed components that are secured together by any known method such as, for example, heat sealing, welding, or press fit. All components that form the housing 2 may be formed separately or as a single unit through processes such as, for example, pouring or injection molding. The housing 2 may be fabricated from, for example, any resilient, insulating material, which material includes thermoplastic material such as, for example, polyethylene. The housing 2 may be any shape, but, as incorporated into sensor 10, is a cylindrical body with the internal and external walls being generally coaxial, as illustrated. The housing 2 may have any suitable dimensions, and as incorporated in micro fuel oxygen sensor 10 may have, for example, a longitudinal length of about 1.25 inches and a diameter of about 1.2 inches. Other housing dimensions will follow from the application for which the sensor is adapted.

The housing 2 includes a first end 22 defining a first opening 24 and a second end 26 defining a second opening 28. The first opening 24 receives the entering stream of gas to be sensed. The first opening 24 may be any size or shape suitable for receiving the gaseous stream, but, as incorporated in the sensor 10, is circular and has a diameter of 0.9 inches. As illustrated, the first opening 24 may be located within a recessed portion 30 of the first end 22 and may be centrally spaced relative to the external wall 3 of the housing 2. The recessed portion 30 may be any size and geometry, but, as incorporated in the sensor 10, is a cylindrical cavity having a diameter of approximately 0.7 inches and is centrally spaced from the external wall 3 of the housing 2. The height of the recessed portion 30 may be substantially equal to the total thickness of the clamp 12, described herein, so that an outer surface of the clamp 12 may be substantially flush with an inner edge of the housing 2 after being placed within the recessed portion 30 of the housing 2 and secured thereto.

The second opening 28 of the housing 2 may be positioned opposite the first opening 24 and may be defined by the external wall 3 of the housing 2. The second opening 28 may be any size or geometry suitable for receiving the back membrane 16 and printed circuit board 18, such as, for example, circular having a diameter of approximately 1.0 inches that is centrally positioned relative to the external wall of the housing 2. The height of the second opening 28 may be substantially equal to the total thickness of the back membrane 16 and the printed circuit board 18 so that a surface of the printed circuit board 18 may be substantially flush with an edge of the housing 2 after being placed over the back membrane 16 and sealed thereto to complete the back portion of the sensor 10.

The internal wall of the housing 2 defines an open ended passage 32 that extends into the housing 2 to form the anode cavity 20, thereby providing fluid communication to the electrolyte in the anode cavity 20 for the gases entering the first opening 24. As adapted for use in sensor 10, the internal wall defining the passage 32 may have a longitudinal length of about 0.93 inches. It will be understood that the anode cavity 20 is an annular chamber defined by the interior dimensions of the housing 2. The anode cavity 20 may be any suitable size and geometry known in the art for containing an amount of electrolyte sufficient for the effective measurement of the entering gaseous stream.

The anode 4 may be formed of any electrically conductive anode material, such as, for example, lead. As adapted for use in sensor 10, the anode 4 may be a solid lead body formed of sintered lead pellets, or may be in the form of a lead wire. The anode 4 may be positioned in the anode cavity 20 in any known manner, such as for example, over or around the internal wall that forms the passage 32 that leads to the anode cavity 20. It will be understood that the anode 4 may be fabricated in a variety of manners, such as, for example by stamping a flat pattern from a sheet of an electrically conductive metal. The anode 4 is electrically connected to external circuitry by, for example, compressed (sintered) pellets around a small coil of silver wire to measure the electrical current produced by the electrochemical reaction occurring at the anode 4.

The cathode 6 may be a concave disc-like member formed of any cathode material know in the art. The cathode 6 may be constructed of, for example, a noble metal such as silver, or a substrate plated with, for example, silver or rhodium. As provided in sensor 10, the cathode 6 may include a concave base having a diameter of 0.9 inches and thickness of 0.01 inches. The cathode base may include a curved contact surface that may be, for example, concave relative to the anode cavity 20 when assembled, and that includes a number of small perforated holes therethrough (not shown). Although those skilled in the art may, upon considering the present disclosure, readily appreciate numerous ways to form the cathode 6, the cathode 6 may be manufactured by photo-chemically etching a flat pattern of the cathode 6 from a sheet of any suitable material, such as, for example, nickel or brass. The cathode 6 is then shaped to include a concave surface, as illustrated, by using one or more of a variety of methods including, for example, the use of a progressive die. The cathode 6 may then be plated with an appropriate cathode material, such as, for example, rhodium, gold or silver. The cathode 6 is electrically connected to external circuitry by, for example, arc welding a small diameter (~0.01 inch) silver wire to the cathode 6 to measure the electrical current produced by the electrochemical reaction occurring at the cathode 6.

The sensing membrane 8 may be positioned adjacent to and in contact with the cathode 6, as illustrated. The sensing membrane 8 may be constructed of any of the various types of hydrophobic, gas permeable materials known in the art. As incorporated in sensor 10, the sensing membrane 8 is formed of a Teflon film. The permeability of the material is such that gas may pass therethrough, but electrolyte solution will not.

The second opening 28 is sealed with a back membrane 16 that allows for expansion or contraction of the electrolyte volume. The back membrane 16 may be any suitable resilient material, such as a thermoplastic, including polyethylene. The back membrane 16 may be sealed to the housing 2 by any means known in the art, but in sensor 10 the back membrane 16 is thermally sealed to the housing 6.

The clamp 22 may be any clamp known to those skilled in the art for effectively retaining the cathode 6 and the sensing membrane 8 in close association with each other and together to provide a positive seal at the first opening 24 of the housing 2. The clamp 22 may be concave relative to the first opening 24 and may include a central woven mesh portion as known in the art that protects the cathode contact 2. The clamp 22 is sized to be received in the recessed portion 30 of the first end 22 and secured therein by any engagement means known in the art. For example, as incorporated into sensor 10, the clamp 12 is fastened over the first opening 24, the cathode 6, and the sensing membrane 8 by threaded fasteners 34. The positive locking action achieved by the fasteners 34 provides the pressure required to effectively seal the sensing membrane 8 to the housing 2 over the first opening 24. The clamp 12 may be constructed of, for example, an elastomer or thermoplastic material that produces sufficient pressure against the sensing membrane 8 and housing 2 to create an effective seal.

The housing 2 further incorporates a space chamber 36 adjacent to the recessed portion 30 of the housing and in fluid communication with the first opening 24. The space chamber 36 is sized to receive an opener 46, described herein. The space chamber 36 may be any size and geometry for receiving the opener 46, but, as incorporated in the sensor 10, is a cylindrical cavity having a diameter of approximately 0.8 inches and a depth of approximately 0.3 inches that is centrally spaced from the external wall of the housing 2. As incorporated into the sensor 10, the space chamber 36 is sized to be larger in diameter than the recessed portion 30 so as to encourage gas flow into the first opening 24 to be sensed.

Figures 6A, 6B:
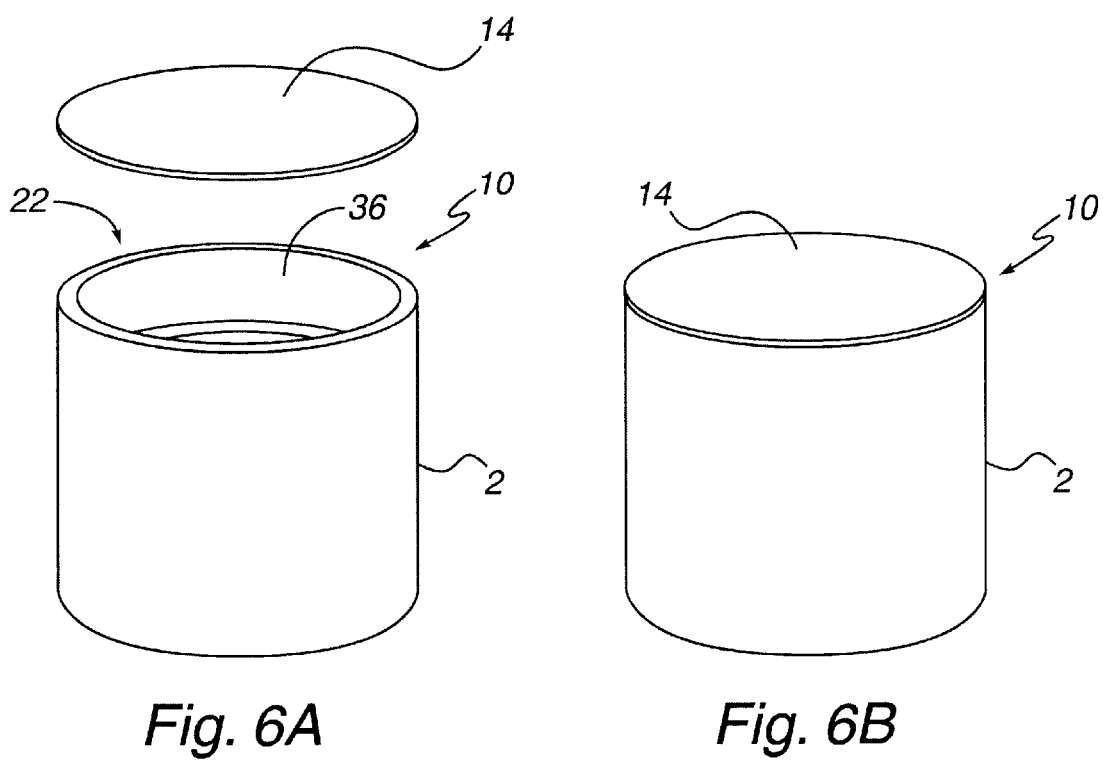
FIG. 6A is an exploded perspective view of the gas sensor of FIG. 6.
FIG. 6B is a perspective view of the gas sensor of FIG. 6.

The protective member 14 is a gas flow inhibitor or resistant member for restricting the flow of gas through the sensor membrane 8, the cathode 6, the first opening 22, and into the anode cavity 20. The protective member 14 may be formed of any relatively non-porous material that restricts or inhibits the flow of gas into the cavity 20, such as, for example, a cellulose material, a plastic, a rubber, or a metal foil. It is also contemplated that the protective member 14 may be formed of any dissolvable barrier material that provides gaseous flow into the anode cavity 20 as a result of a physical or chemical change in the material by, for example, variation in gas measuring operating parameters such as, for example, temperature or pressure changes. For example, the protective member 14 may be formed of a frozen material, such as, for example, ice that melts as a result of an increase in temperature within the gas analyzer to provide gas flow into the first opening 22. As incorporated into the sensor 10, the protective member 14 may be a type 304 stainless steel foil membrane having a thickness of 0.0015 inches, so that the membrane can be easily pierced by the opener 46, described herein. The protective member 14 can be any cross-sectional shape and size to restrict the flow of gas into the anode cavity 20. As incorporated into the sensor 10, and as best illustrated in FIGS. 6A and 6B, the protective member 14 is a foil membrane having a circular cross-section having approximately the same diameter as the diameter of the housing 2 to cover the first end 22 and the space chamber 36. The protective membrane 14 may, but need not, cover the entire first end 22 of the housing 2, as illustrated. Indeed, the protective member 14 need only be of sufficient size to seal the first opening 24 from the flow of gas into the anode cavity 20. The protective member 14 may be secured to the first end 22 of the housing by any suitable fastening means known in the art, such as, for example, adhesives, press fit, heat seal, mechanical fasteners, threaded engagement, or combinations thereof.

FIGS. 7 and 8 illustrate a cell holder 40 or cell block as a portion of a fuel cell or gas analyzer, and one method of assembling the gas sensor 10 and the cell holder 40 for gas analysis. The cell holder 40 may include a cavity portion 42 and a cap portion 44. The cell holder 40 may be any size and geometry suitable for receiving and containing the gas sensor 10, but as illustrated in the Figures, is cylindrical with the internal and external walls being generally coaxial. As incorporated into the present invention, the cell holder 40 is a cylindrical body having a longitudinal length of about 4.0 inches and a diameter of about 2.25 inches. All components that form the cell holder 40 may be formed separately or as a single unit through processes such as, for example, pouring or injection molding. The cell holder 40 may be fabricated from, for example, any resilient material, including thermoplastic material such as, for example, polyethylene.

The cavity portion 42 may be any size and geometry for receiving the gas sensor 10, and may, but need not be, the same geometry as the gas sensor 10. The cavity portion 42 should be sized slightly larger than the gas sensor 10 to provide adequate gas flow around the sensor housing 2. The cavity portion 42 may be a single formed component or may be separately formed components that are secured together by any known method such as, for example, heat sealing, welding, or press fit. As incorporated into the present invention, the cavity portion 42 is a cylindrical holder having a longitudinal length of approximately 3.3 inches and a diameter at the first end 43 of approximately 1.25 inches for receiving the gas sensor 10. The cavity portion 42 includes a gas supply inlet and a gas outlet for receiving and exiting, respectively, pressurized gas to be measured. As known in those skilled in the art, the cavity portion 42 includes electrical contacts (not shown) on an inner top surface that defines the cavity for engagement with the printed circuit board 18 of the gas sensor 10.

Figure 9:
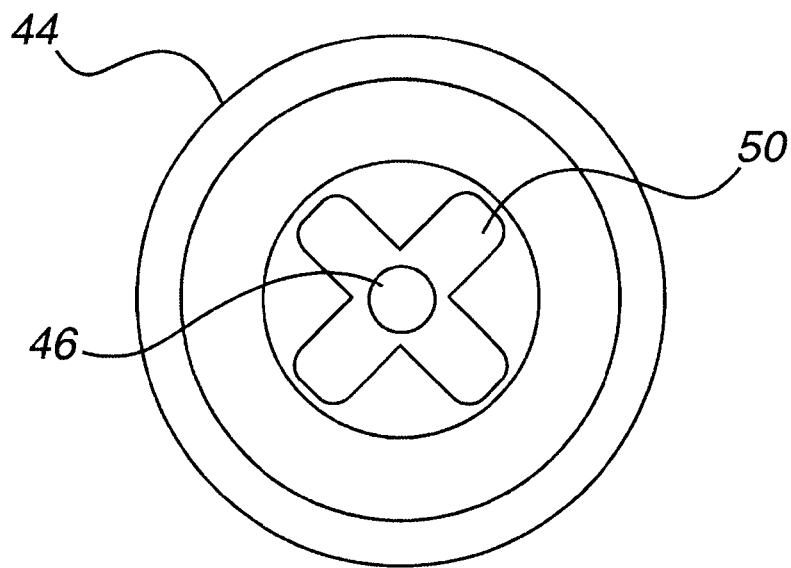
FIG. 9 is top plan view of one embodiment of the cap portion and opener of the present invention.
Figure 10:
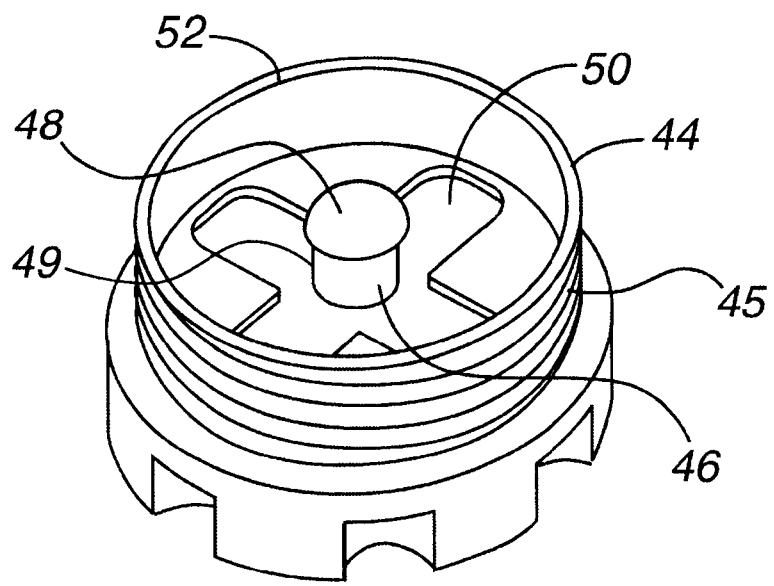
FIG. 10 is a perspective view of the cap portion of FIG. 9.
Figure 11:
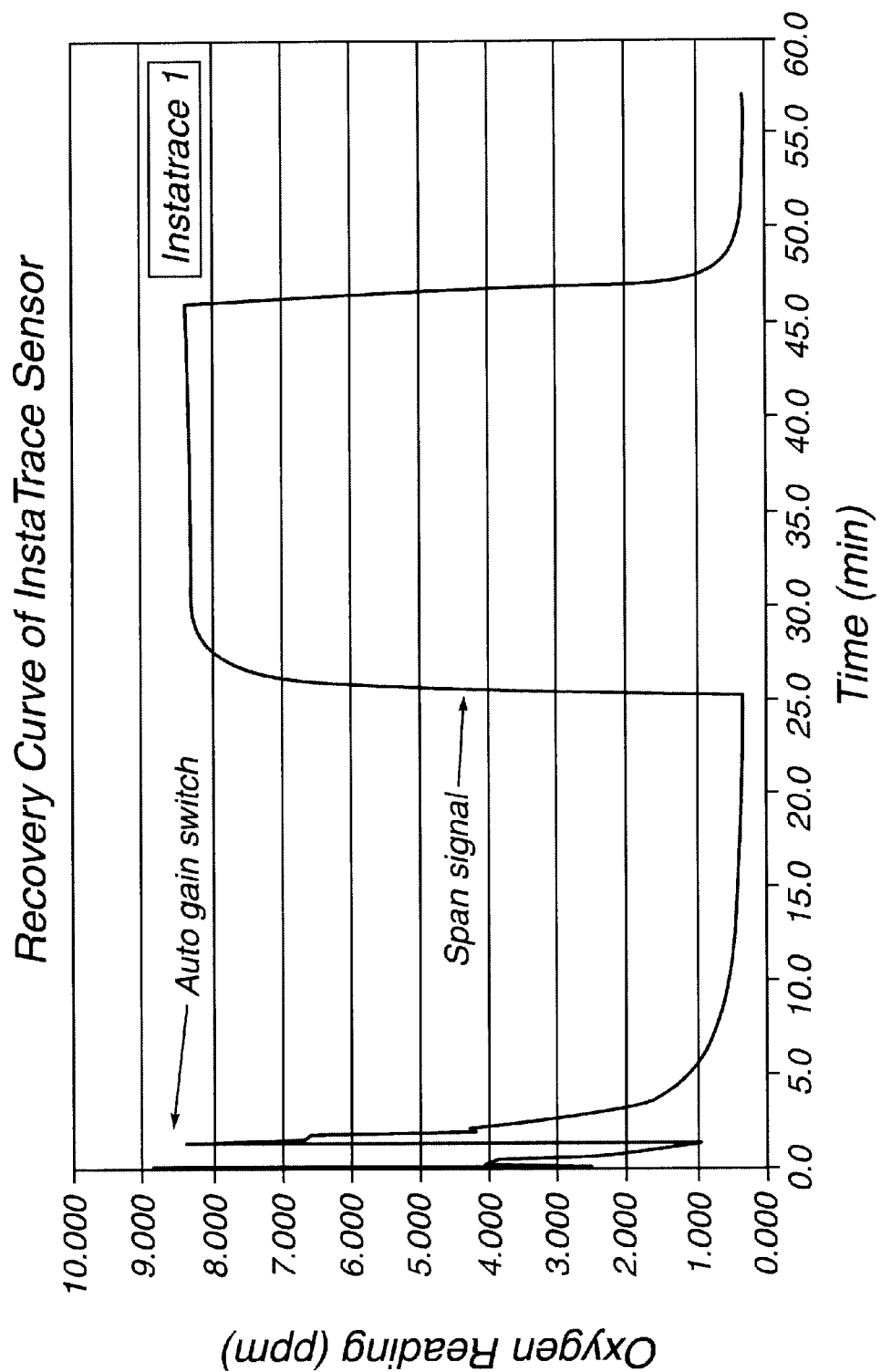
FIG. 11 is a recovery curve plotting oxygen reading versus time of a gas sensor of the present invention.
Figure 12:
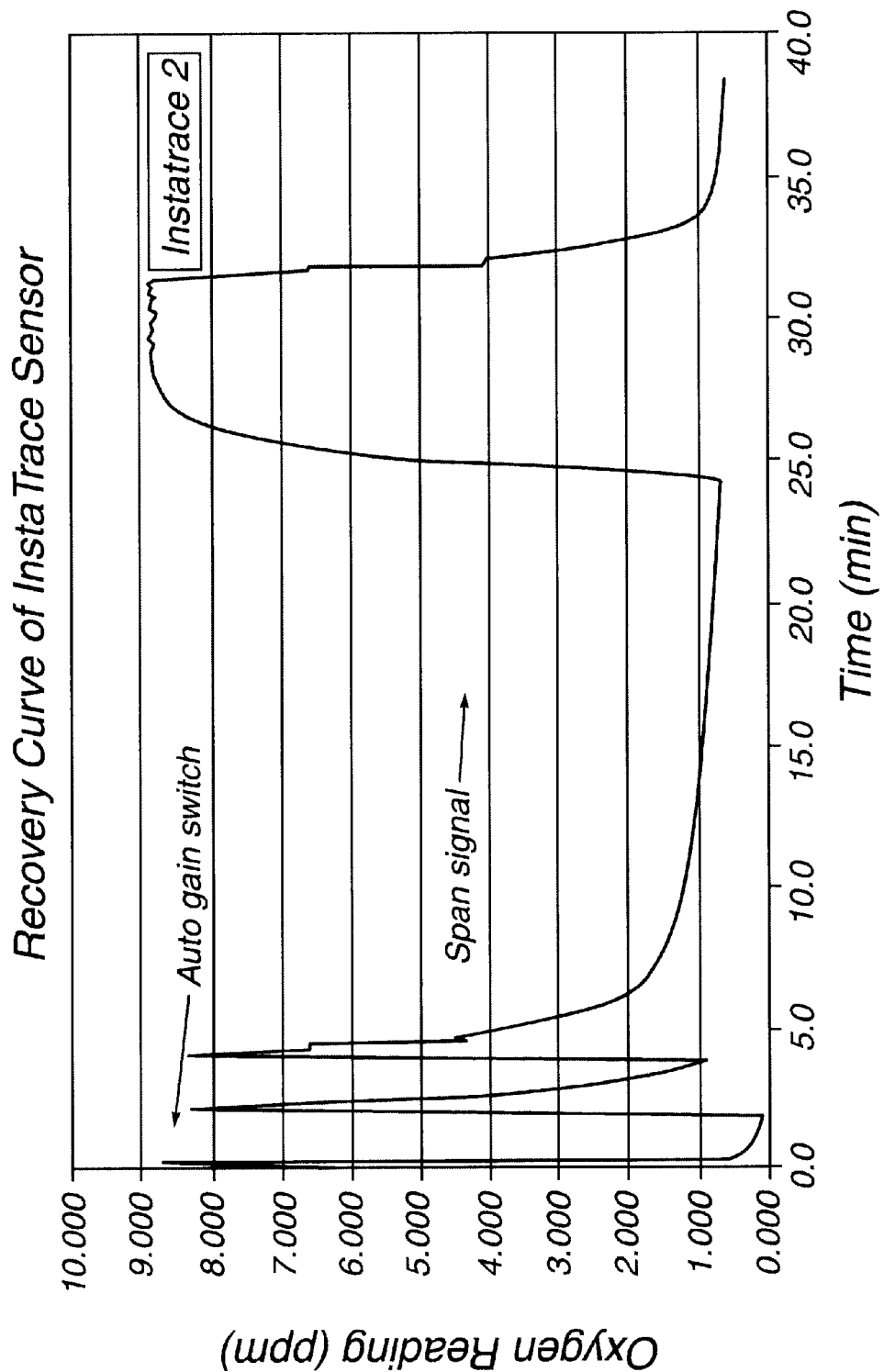
FIG. 12 is a recovery curve plotting oxygen reading versus time of a gas sensor of the present invention.
Figure 13:
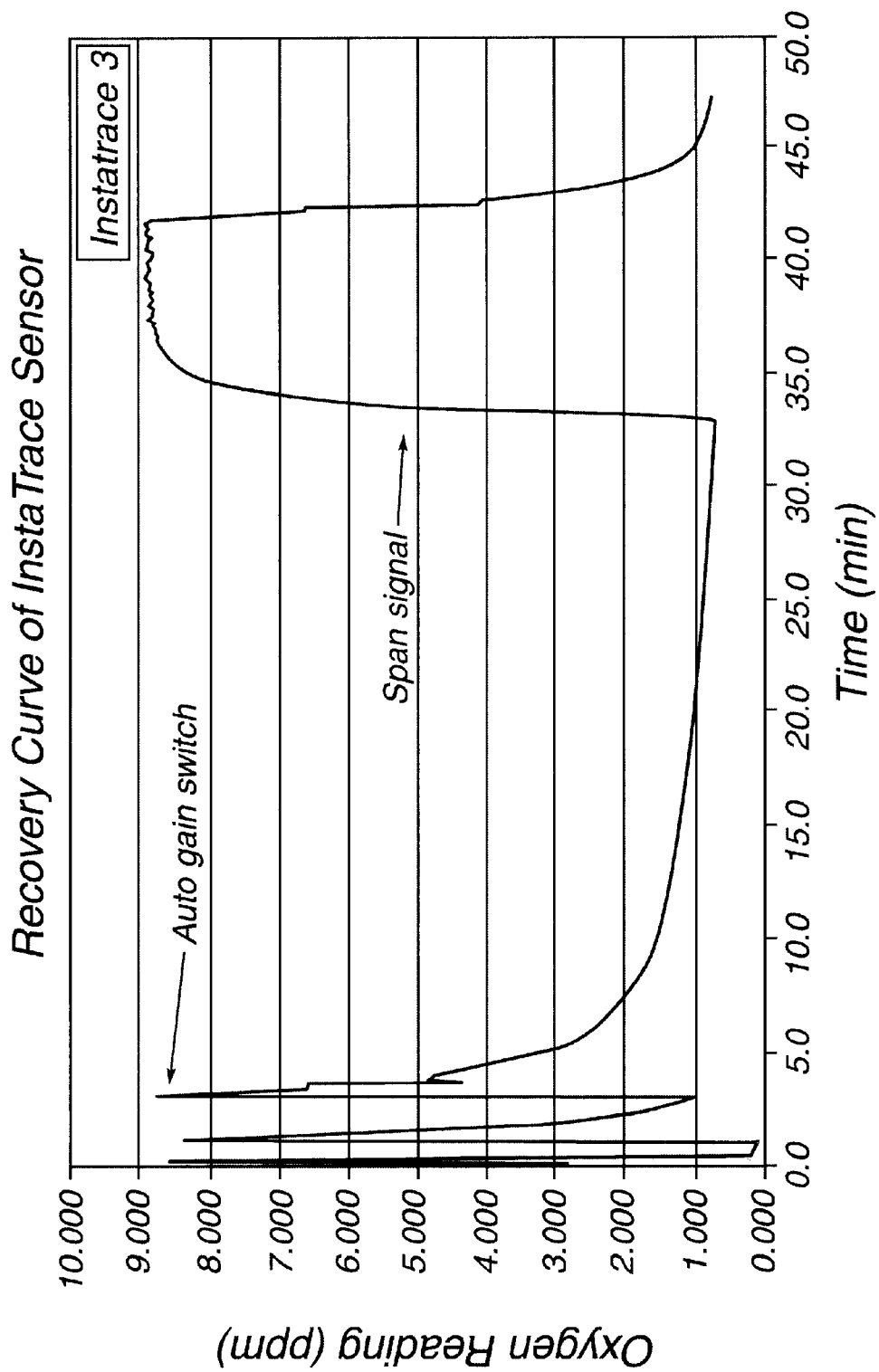
FIG. 13 is a recovery curve plotting oxygen reading versus time of a gas sensor of the present invention.
Figure 14:
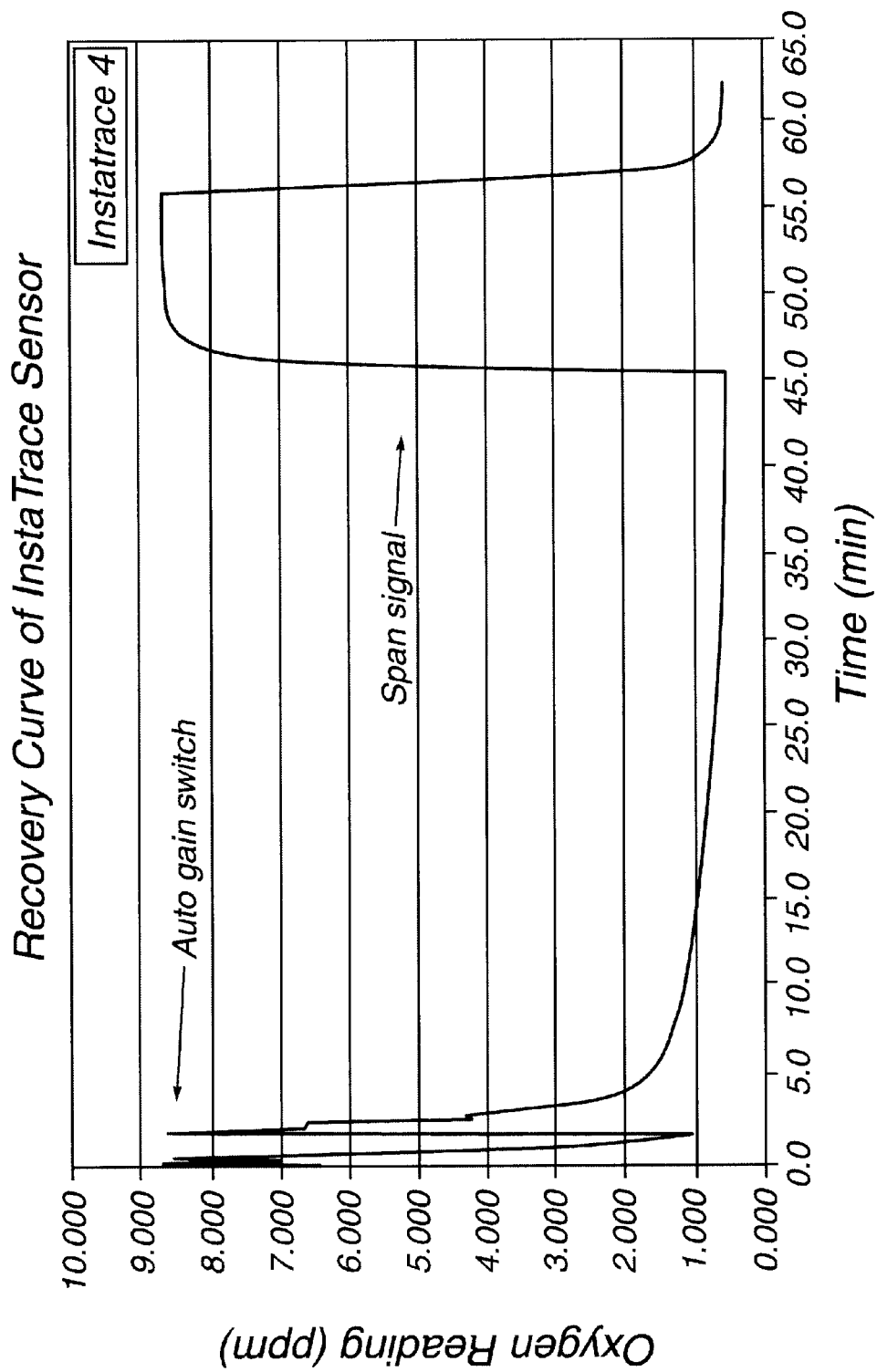
FIG. 14 is a recovery curve plotting oxygen reading versus time of a gas sensor of the present invention.
Figure 15:
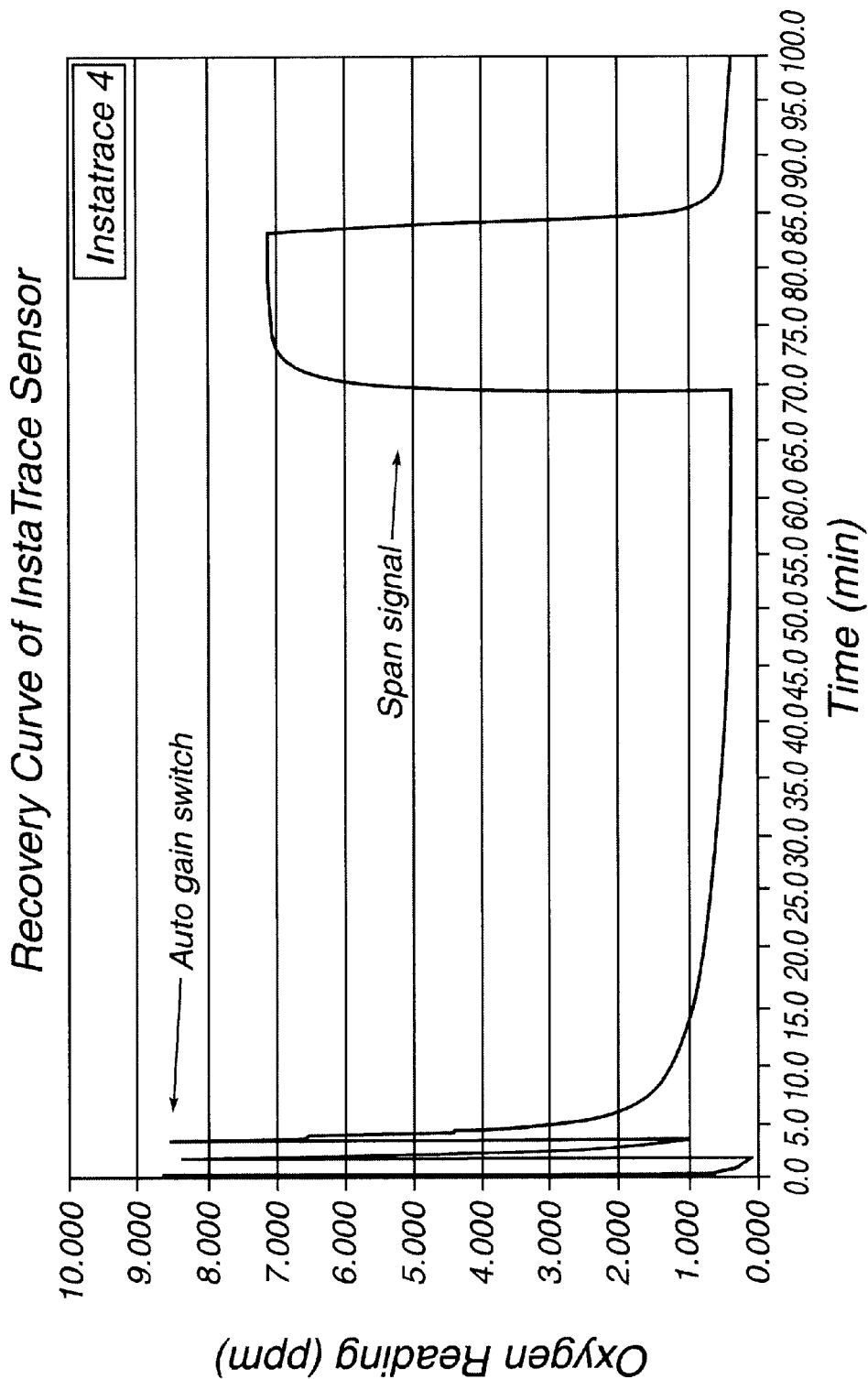
FIG. 15 is a recovery curve plotting oxygen reading versus time of a gas sensor of the present invention.
Figure 16:
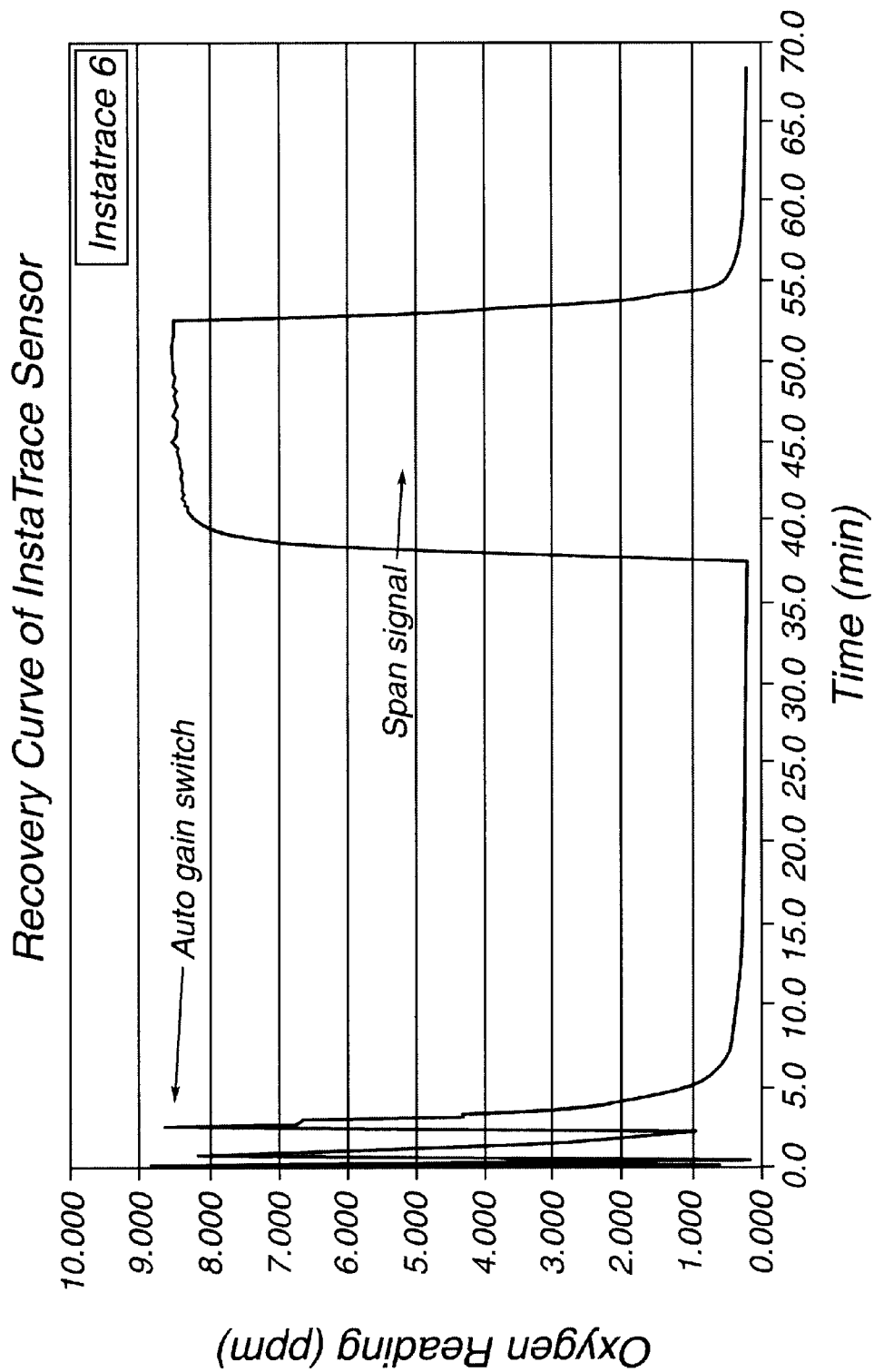
FIG. 16 is a recovery curve plotting oxygen reading versus time of a gas sensor Of the present invention.
Figure 17:
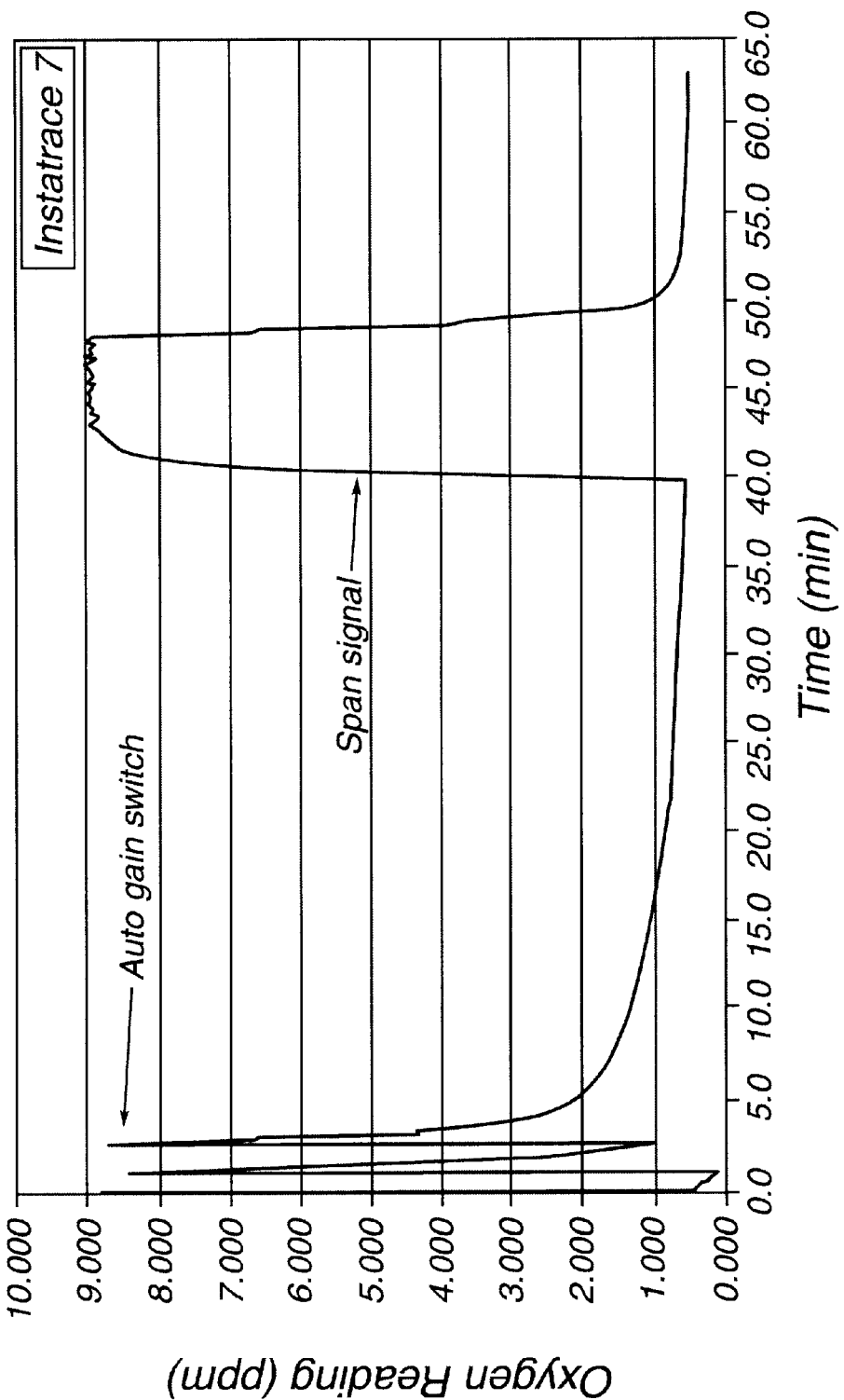
FIG. 17 is a recovery curve plotting oxygen reading versus time of a gas sensor of the present invention.
Figure 18:
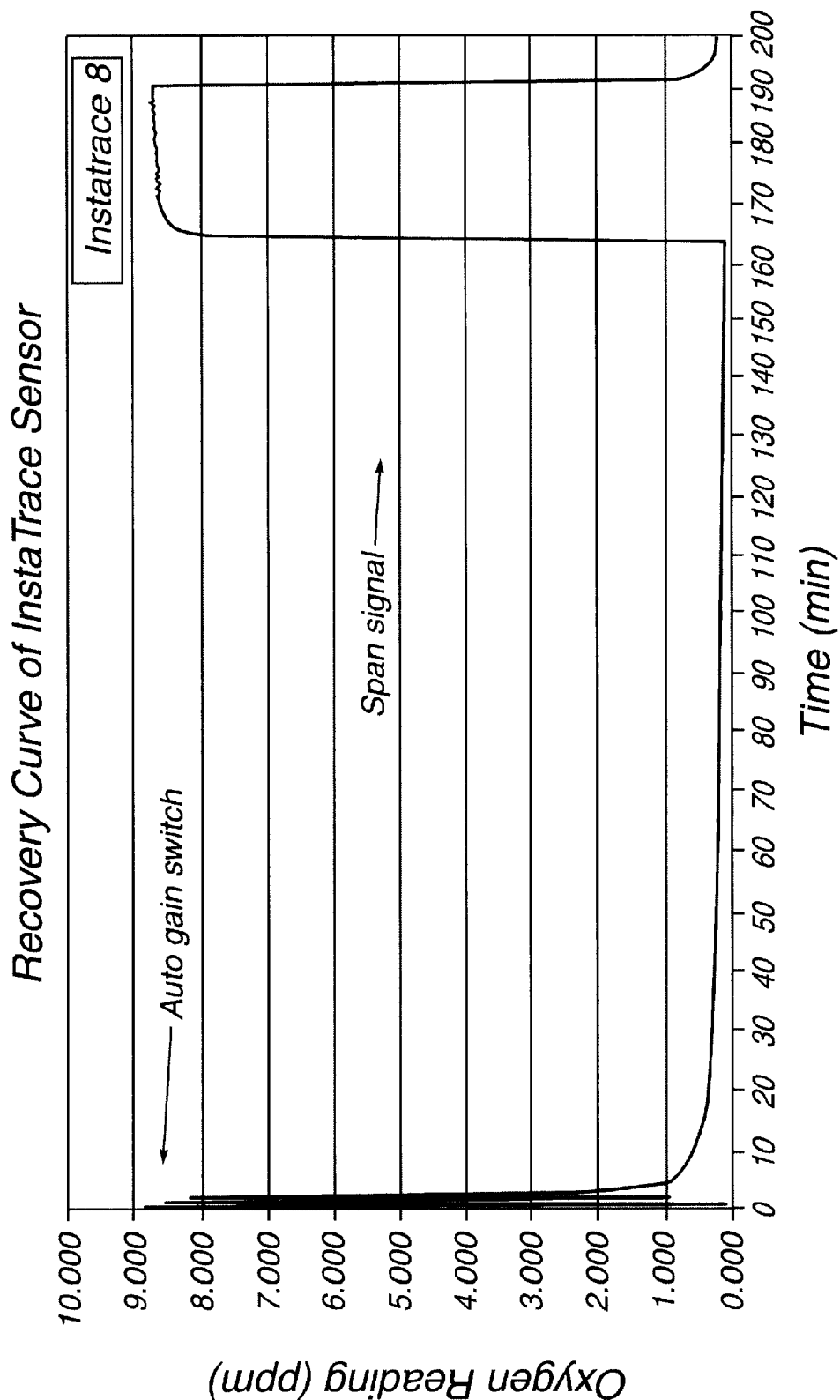
FIG. 18 is a recovery curve plotting oxygen reading versus time of a gas sensor of the present invention.
Figure 19:
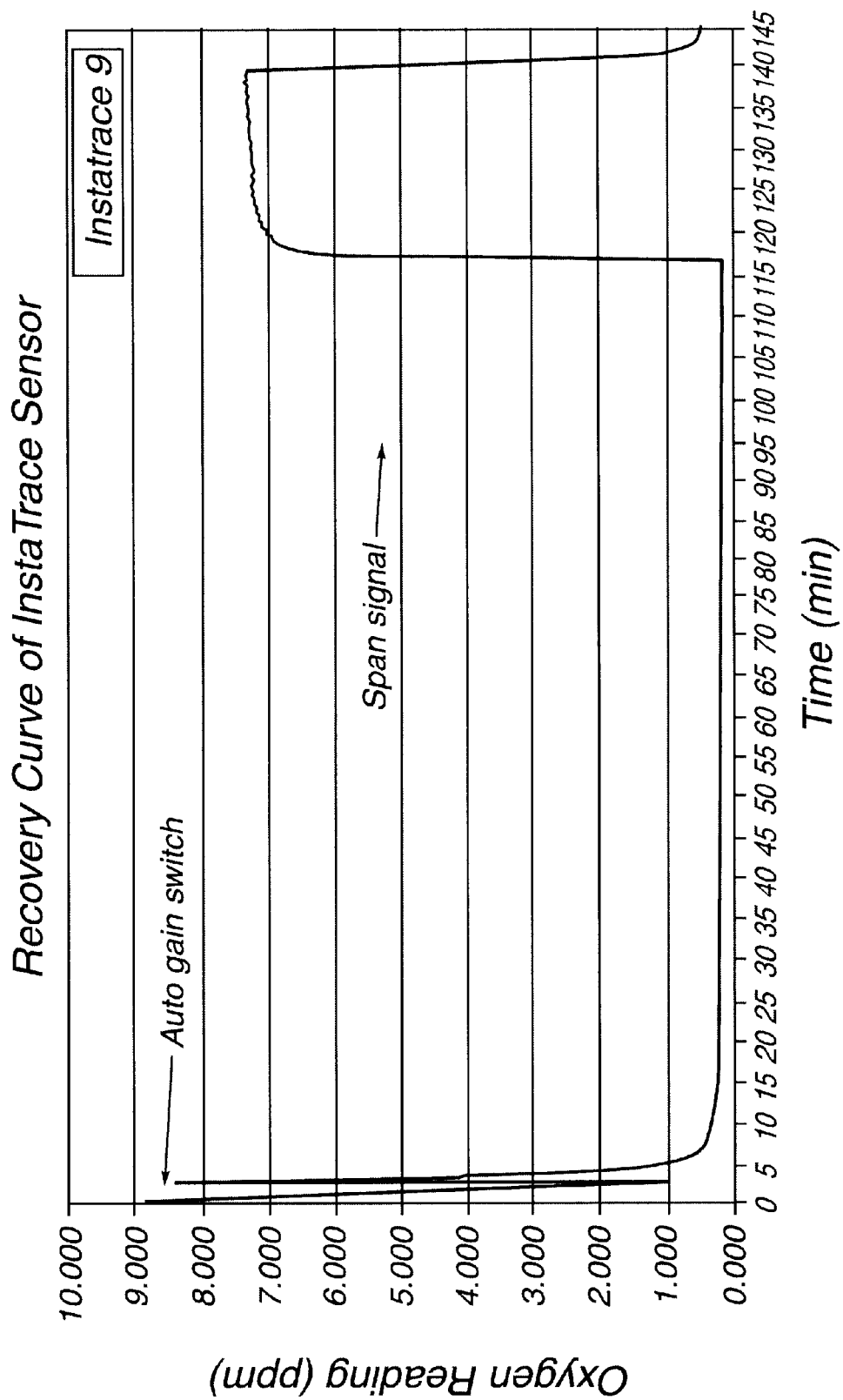
FIG. 19 is a recovery curve plotting oxygen reading versus time of a gas sensor of the present invention.
Figure 20:
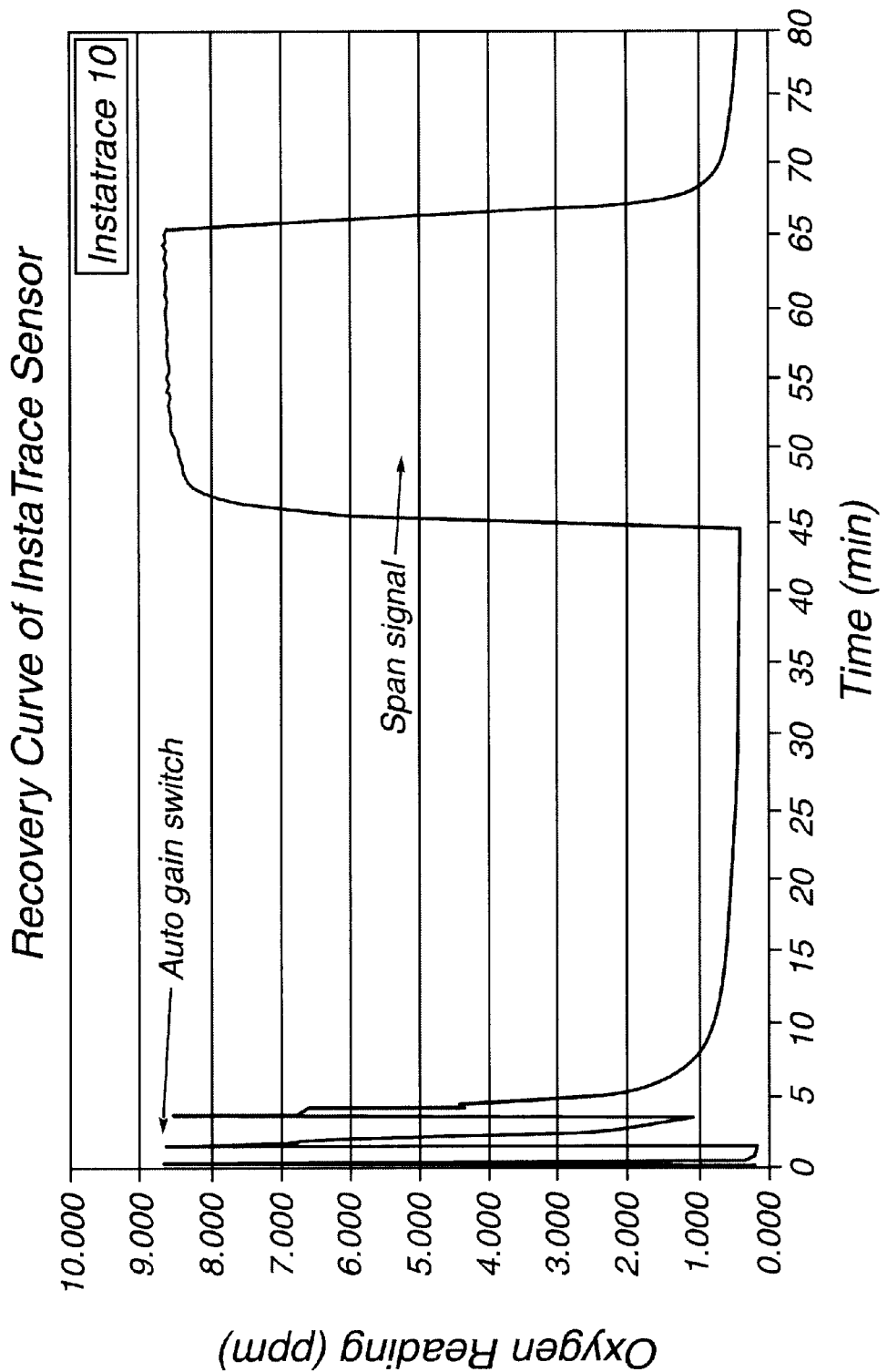
FIG. 20 is a recovery curve plotting oxygen reading versus time of a gas sensor of the present invention.

The cell holder 40 may include a cap portion 44 that securably engages the cavity portion 42 to enclose the gas sensor 10 therein (FIG. 8). Any engagement means may be used to secure the cavity portion 42 to the cell holder 44, such as, for example, a threaded connection. In this form, the first end 43 of the cavity portion 42 is threaded, and the cap portion 44 includes a mating threaded portion 45 (FIG. 10) to provide threaded engagement therewith. As illustrated in FIG. 10, it is contemplated that the cap portion 44 may include a peripheral rim portion 52 defining an inside diameter similar in size and geometry as the cavity portion 42 for receiving a portion of the sensor 10. For example, the rim portion 52 defining the cavity may have a diameter of 1.25 inches and a depth of 0.63 inches. This design allows the sensor 10 to be held in place by both the cavity portion 42 and the cap portion 44 until both sections are fastened together. In the alternative, as illustrated in FIGS. 7–9, the cap portion 44 may be substantially flat, but for the opener 46 and the recessed portion 50 described below. As illustrated in FIGS. 9 and 10, the cap portion 44 may further include a recessed portion 50 for providing gas flow channels for entering gas to efficiently and effectively enter the gas sensor 10 when the sensor 10 is contained within the cell holder 40. As illustrated, the recessed portion 50 takes the form of X-shaped flow channels, but may be any configuration to provide additional flow into the sensor 10.

As further illustrated in FIGS. 7–10, the cell holder 40 may include an opener 46 for engaging the protective member 14 and providing fluid communication between the external portion of the gas sensor 10 and the internal portion of the gas sensor 10, generally defined by the space chamber 36, the first opening 24, the passage 32, and the anode cavity 20. As best shown in FIG. 8, the opener 46 may be a projection that is secured to, and may be integrally formed with, the cap portion 44. In this way, when the cavity portion 42 is secured to the cap portion 44, the opener 46 engages the protective member 14 to provide a gas pathway into the sensor 10 from an area external to the gas sensor 10. It is contemplated that in an alternative construction, the opener 46 may be secured to the cavity portion 42, such as, for example, in a construction where the gas sensor 10 is rotated 180 degrees and positioned within the cell holder 40 such that the printed circuit board 18 is adjacent to the cap portion 44. The opener 46 may be any device that breaks or removes a portion of the protective member 14 to provide gas flow into the sensor 10. As incorporated in the present invention, the opener 46 is a centrally positioned projection for piercing the protective member 14. In the embodiment illustrated in the Figures, the height of the opener 46 should not exceed the depth of the space chamber 36, so that when the cavity portion 42 is engaged to the cap portion 44 the opener 46 does not damage or, otherwise, contact the clamp 12, the sensing membrane 8, or the cathode 6. As incorporated in the present invention, and as best illustrated in FIGS. 7, 8 and 10, the opener 46 may be a mushroom-shaped punch having a piercing head 48 and a cylindrical stem 49 that is integrally formed with the cap portion 44. The opener 46 may, but need not, have a piercing head 48 that has a larger cross-sectional area than the cross-section area of the stem 49. In this regard, it is contemplated that the opener 46 may take many different geometries for creating a gas pathway into the sensor 10 such as, for example, conical, cylindrical, arrow-shaped, diamond-shaped, and the like. For example, the opener 46 may be a cylindrical shaped member having a diameter of approximately 0.25 inches and a height of approximately 0.4 inches. The opener 46 may be formed of any resilient material that can effectively break or remove a portion of the protective membrane 14, such as, for example, a metal or a plastic. In addition, it is contemplated that more than one opener 46 may be secured to the cap portion 44 to provide additional air flow pathways (or a single large air flow pathway) into the sensor 10.

Accordingly, the present invention provides an approach that may be used alone or in combination with conventional packaging to limit the exposure of the sensor 10 to gas, particularly to high concentrations of oxygen in ambient air. In particular, the present invention restricts the flood of air and other gases into the sensor during the transition period, first beginning when the gas sensor is removed from the protective packaging until installation into the gas analyzer. The protective member 14 provides a seal over the first opening 24 of the housing 2 that substantially restricts the flow of gas into the sensor 10 until the sensor 10 is installed into the cell holder 40 of the analyzer. Accordingly, the amount of air to which the sensor 10 is exposed during the transition period is substantially reduced. Accordingly, the amount of gas that diffuses into the electrolyte solution that would, otherwise, adversely affect the accurate and precise measurement of low concentrations of gas at the early stages of operation, is greatly diminished. As a result, the recovery time required for the excess gas to slowly diffuse from the electrolyte is substantially reduced.

In order that those skilled in the art may better understand how the invention may be practiced, the following examples are given by way of illustration and not by way of limitation on the invention as defined by the claims. As will be apparent upon inspection of the below test results, the sensor 10 of the present invention substantially reduces the time required to accurately measure low concentrations of gas after installation into an analyzer, as compared to the conventional sensor that does not incorporate the protective member 14 and associated cell holder assembly.

EXAMPLE 1

A system of the present invention was employed that consisted of a B2 C style sensor, manufactured by Teledyne Analytical Instruments ("TAI"), City of Industry, Calif. with a B2 to L2 adapter, also manufactured by TAI, City of Industry, Calif. without flow through holes on the side epoxied using 5 minute epoxy onto the B2 sensor. The top of the sensor was covered with an adhesive backed stainless steel foil. The cell holder incorporated a small screw-like projection centrally positioned in the cap portion therein so that upon engagement with the cavity portion of the cell holder the screw-like projection punctured the foil, leaving a gas flow path to the cathode.

The sensor was constructed as described above in the glovebox in a chemistry lab. The oxygen concentration within this glovebox as reported by a TAI Model 311 Analyzer on the vent side was approximately 300 ppm when the modification of the sensors to this system began. The modification of the sensors took approximately 2 hours from start to removal (including epoxy cure time) from the glovebox in the conventional double bagging system.

The sensor was installed in a TAI 3000TAXL unit in a chemistry lab. The cell block was flooded with nitrogen at approximately 2 liters/min (fall flow) prior to installation. Thereafter the sensor was installed into the analyzer. Within approximately 20 seconds, the oxygen sensor reading spiked upwardly to approximately 170 ppm, and then began to decrease. The time the sensor was out in air was approximately 10 seconds.

Data taken manually is indicated in Table 1, below:

TABLE 1

| Elapsed time after installation +20 seconds | Reading in ppm |
|---|---|
| 50s | 100 |
| 1:35 | 69 |
| 2:53 | 36 |
| 3:16 | 31.2 |
| 3:39 | 27.0 |
| 4:15 | 21.4 |
| 5:11 | 16.9 |
| 7:30 | 11.9 |
| 7:45 | 11.3 |
| 8:17 | 10.7 |
| 13.52 | 6.99 |
| 29:34 | 3.46 |
| ~1:00:00 | 2.15 |
| 1:6:58 | 1.83 |
| 1:15:08 | 1.53 |

The data provided in Table 1 indicates that the sensor of the present invention substantially reduced the recovery time from air exposure of disposable electrochemical cells. The recovery time from air exposure is typically considerably longer without such a system. In contrast with conventional methods that require a recovery time of approximately 3 hours to achieve 2 ppm, the results of Table 1 clearly show that an embodiment constructed according to the present invention allows recovery to 2 ppm to occur in approximately 1 hour. It is believed that further improvements may reduce the time requirements by additional amounts.

EXAMPLE 2

Two sensors of the present invention were fabricated as described herein, tested for recovery time, and compared to conventional sensors. Sensor 1 of the present invention was removed from the double bag system to be inserted into the cell block. However, the sensor did not fit into the cell block due to excess sealing epoxy from the baffle on the side of the sensor. This excess epoxy was removed, during which time the sensor was exposed to air for approximately 2 minutes. The sensor recovered to 1 ppm in approximately 1 hour when inserted into a model 3000TA analyzer. Sensor 2 of the present invention was tested in the same manner as Sensor 1. Recovery of the sensor to less than 1 ppm was, again, achieved in approximately 1 hour.

Two conventional sensors were tested from the same B2 C production run as Sensor 1 and Sensor 2. The comparative tests employed the same procedures described above. Tests results from the conventional sensors indicated that recovery to less than 1 ppm occurred in approximately 4.2 hours for the first conventional sensor, while recovery to approximately 2 ppm took place in about 3 hours for the second conventional sensor.

The comparative results clearly shows that the sensors of the present invention substantially reduce the recovery time relative to conventional sensors.

As further illustrated in FIGS. 11–20, several additional gas sensors of the present invention were constructed as described herein and tested to determine their recovery time. The sensors were stored in convention double-bag containers or standard oxygen absorbant containers for 20 days prior to removal and testing. As illustrated in the Figures, oxygen levels of well below 1 ppm were obtained within in as little as 5 minutes (FIGS. 16 and 19) while all gas sensors had achieved this level and were available for testing within no more than 30 minutes.

Although the foregoing description has necessarily presented a limited number of embodiments of the invention, those of ordinary skill in the relevant art will appreciate that various changes in the configurations, details, materials, and arrangement of the elements that have been herein described and illustrated in order to explain the nature of the invention may be made by those skilled in the art, and all such modifications will remain within the principle and scope of the invention as expressed herein in the appended claims. In addition, although the foregoing detailed description has been directed to an embodiment of the gas sensor of the invention in the form of a micro fuel cell oxygen sensor, it will be understood that the present invention has broader applicability and, for example, may be used in connection with the construction of all gas sensors. All such additional applications of the invention remain within the principle and scope of the invention as embodied in the appended claims.

What is claimed is:

1. A gas sensor, comprising:
   a housing including a cavity, the housing defining an opening into the cavity; and
   a gas flow resistant member engaging the housing and being sealably positioned over the opening, the gas flow resistant member being formed of a material at least a portion of which is breakable, removable, dissolvable, or meltable to define a gas pathway from an area external to the sensor into the cavity via the opening through which gas is sensed.

2. The gas sensor of claim 1, further including:
   a first electrode positioned within the cavity;
   a second electrode positioned at the opening; and
   a sensing membrane positioned at the opening adjacent to the second electrode;
   the gas flow resistant member positioned adjacent to the second electrode and the sensing membrane.

3. The gas sensor of claim 1, wherein the gas flow resistant member is a gas flow resistant membrane.

4. The gas sensor of claim 3, wherein the gas flow resistant membrane is formed of a stainless steel foil.

5. The gas sensor of claim 1, wherein the housing defines a space chamber positioned adjacent to the opening, the gas flow resistant member being sealably positioned adjacent to the space chamber.

6. The gas sensor of claim 5, wherein the space chamber is sized to receive a gas flow resistant member opener.

7. The gas sensor of claim 6, wherein the opener is a piercing member.

8. The gas sensor of claim 1, wherein the opening is positioned in a recessed portion defined by the housing, the housing further defining a space chamber adjacent to the recessed portion, the gas flow resistant member being sealably positioned over the space chamber.

9. A gas sensor, comprising:
   a housing including a cavity, the housing having a first end defining an opening into the cavity;
   a first electrode positioned within the cavity;
   a second electrode positioned at the opening;
   a sensing membrane positioned at the opening adjacent to the second electrode;
   a gas resistant member engaging the first end of the housing and being sealably positioned over the opening, the gas flow resistant member being formed of a material at least a portion of which is breakable, removable, dissolvable, or meltable to define a gas pathway from an area external to the sensor into the cavity via the opening through which gas is sensed.

10. The gas sensor of claim 9, wherein the opening is positioned in a recessed portion defined by the housing, the housing further defining a space chamber adjacent to the recessed portion, the resistant member sealably positioned over the space chamber.

11. The gas sensor of claim 10, wherein the space chamber is sized to receive a piercing member.

12. A gas sensor, comprising:
   a housing including a cavity, the housing defining an opening into the cavity; and
   means for restricting the flow of a gas into the opening, the means engaging the housing during a transition period, and thereafter providing fluid communication for gases entering the opening to the cavity.

13. The gas sensor of claim 12, further including:
   a first electrode positioned within the cavity;
   a second electrode positioned at the opening; and
   a sensing membrane positioned at the opening adjacent a first side of the second electrode;
   the means for restricting being positioned over the second electrode and the sensing membrane.

14. The gas sensor of claim 12, wherein the housing defines a space chamber positioned adjacent to the opening, the resistant member being sealably positioned over the space chamber.

15. The gas sensor of claim 14, wherein the space chamber is sized to receive a resistant member opener.

16. The gas sensor of claim 15, wherein the resistant member opener is a piercing member.

17. The gas sensor of claim 15, wherein the resistant member is a gas flow resistant membrane formed of a stainless steel foil.

18. A fuel cell comprising a gas sensor, said gas sensor including:
   a housing having a cavity, the housing defining an opening into the cavity; and
   a gas flow resistant member engaging the housing and being sealably positioned over the opening, the gas flow resistant member being formed of a material at least a portion of which is breakable, removable, dissolvable, or meltable to define a gas pathway from an area external to the sensor into the cavity via the opening through which gas is sensed.

19. The fuel cell of claim 18, wherein the gas sensor further includes:
   a first electrode positioned within the cavity;
   a second electrode positioned at the opening; and
   a sensing membrane positioned at the opening adjacent to the second electrode;
   the gas flow resistant member positioned over the second electrode and the sensing membrane.

20. The fuel cell of claim 19, wherein the gas flow resistant member is a gas flow resistant membrane.

21. The fuel cell of claim 19, wherein the housing defines a space chamber positioned adjacent to the opening, the gas flow resistant member being sealably positioned over the space chamber.

22. The fuel cell of claim 21, wherein the space chamber is sized to receive a gas flow resistant member opener.

23. The fuel cell of claim 22, wherein the gas flow resistant member opener is a piercing member.

24. The fuel cell of claim 19, further including a cell block, the cell block comprising:
   a cavity portion; and
   a cap portion, the cap portion removably secured to the cavity portion for containing the gas sensor.

25. The fuel cell of claim 24, wherein the cap portion includes a piercing member that securably engages the cap portion.

26. The fuel cell of claim 25, wherein the piercing member is integrally formed with the cap portion.

27. The fuel cell of claim 25, wherein the cap portion includes a peripheral rim defining a cavity therein for receiving at least a portion of the gas sensor.

28. The fuel cell of claim 27, wherein the peripheral rim is threaded to provide threaded engagement with the cavity portion.

29. The fuel cell of claim 25, wherein the cap portion further includes a recessed flow channel.

30. A system for sensing gas, comprising:
   a gas analyzer defining a cavity;
   a cell block sized to be received into the cavity; and
   a gas sensor, the sensor sized to be received in the cell block, the sensor including a housing defining a sensor cavity, the housing further defining an opening into the sensor cavity, the sensor further including a gas flow resistant member engaging the housing and sealably positioned over the opening, the gas flow resistant member being formed of a material at least a portion of which is breakable, removable, dissolvable, or meltable to define a gas pathway from an area external to the sensor into the cavity via the opening through which gas is sensed.

31. The system of claim 30, wherein the system includes a gas flow resistant member opener.

32. The system of claim 31, wherein the cell block comprises:
   a cavity portion; and
   a cap portion, the cap portion being removably secured to the cavity portion for receiving the gas sensor, the gas flow resistant member opener being in engagement with the cap portion.

33. The system of claim 32, wherein the gas flow resistant member opener is integral with the cap portion.

34. The system of claim 33, wherein the gas flow resistant member opener is a piercing member having a piercing head.

35. A method of inhibiting the flow of gas into a gas sensor, the method comprising:
   securing a gas flow resistant member to the gas sensor, the gas sensor including a housing defining a cavity, the housing further defining an opening into the cavity, the gas flow resistant member being sealably positioned over the opening, the gas flow resistant member being formed of a material at least a portion of which is breakable, removable, dissolvable, or meltable to define a gas pathway from an area external to the sensor into the cavity via the opening through which gas is sensed.

36. The method of claim 35, wherein the housing defines a space chamber adjacent to the opening, the resistant member sealably positioned over the space chamber.

37. The method of claim 36, wherein the space chamber is sized to receive a gas flow resistant member opener.

38. The method of claim 37, wherein the gas flow resistant member opener is a piercing member.

39. The method of claim 36, wherein securing the gas flow resistant member is performed by at least one of adhesive, heat seal, press fit, and mechanical fasteners.

40. A method of performing gas analysis on a gaseous stream, comprising:
   inserting a gas sensor into a cell block, the gas sensor having a housing including a cavity, the housing defining an opening into the sensor cavity, the opening sealed by a gas flow resistant member to restrict a flow of gas into the housing cavity from a region exterior to the housing cavity during a transition period;

providing fluid communication between the exterior region of the sensor cavity and the sensor cavity through the opening;

inserting a cell block into the analyzer cavity; and performing gas analysis on the gaseous stream.

41. The method of claim 40, wherein the cell block comprises:

a cavity portion; and a cap portion, the cap portion being removably secured to the cavity portion for receiving the gas sensor, the cap portion further including a gas flow resistant member opener in engagement with the cap portion.

42. The method of claim 41, wherein providing fluid communication is performed by insertion of the opener through the gas flow resistant member.

43. The method of claim 42, wherein the opener is a piercing member.

44. The method of claim 43, wherein the piercing member is integral with the sensor holder.

45. The method of claim 42, wherein the gas sensor further includes a space chamber positioned adjacent to the opening such that the opener enters the space chamber upon passing through the gas flow resistant member.

* * * * *

UNITED STATES PATENT AND TRADEMARK OFFICE
CERTIFICATE OF CORRECTION

PATENT NO. : 6,524,740 B1
DATED : February 25, 2003
INVENTOR(S) : Stephen H. Broy and Austin J. Patrizio It is certified that error appears in the above-identified patent and that said Letters Patent is hereby corrected as shown below:

Column 4,
Line 27, delete "is" before "lower"

Column 10,
Line 62, delete "fall" and substitute therefore with -- full --

Signed and Sealed this

Nineteenth Day of August, 2003

JAMES E. ROGAN
*Director of the United States Patent and Trademark Office*